US006462254B1

(12) United States Patent
Vernachio et al.

(10) Patent No.: US 6,462,254 B1
(45) Date of Patent: Oct. 8, 2002

(54) DUAL-TAGGED PROTEINS AND THEIR USES

(75) Inventors: John Vernachio, Canton, GA (US); Jackie Papkoff, Palo Alto, CA (US)

(73) Assignees: Valentis, Inc., Burlingame, CA (US); Pfizer, Inc., New York, NY (US)

( * ) Notice: Subject to any disclaimer, the term of this patent is extended or adjusted under 35 U.S.C. 154(b) by 0 days.

(21) Appl. No.: 09/272,068

(22) Filed: Mar. 18, 1999

Related U.S. Application Data

(60) Provisional application No. 60/079,125, filed on Mar. 23, 1998.

(51) Int. Cl.$^7$ .......................... C12P 21/00; C12P 21/04; C12N 15/63
(52) U.S. Cl. ................. 800/4; 435/69.7; 435/69.8; 435/320.1; 530/413
(58) Field of Search ................ 536/23.4, 23.5, 536/25.32; 435/455, 69.1, 69.7, 69.8; 800/3, 4; 530/413

(56) References Cited

U.S. PATENT DOCUMENTS

| | | | |
|---|---|---|---|
| 4,851,341 A | | 7/1989 | Hopp et al. ................ 435/69.7 |
| 5,047,513 A | | 9/1991 | Döbeli et al. .............. 530/412 |
| 5,283,179 A | | 2/1994 | Wood ........................... 435/8 |
| 5,643,731 A | | 7/1997 | Bosslet et al. ............... 435/7.1 |
| 5,652,128 A | | 7/1997 | Jarvik ........................ 435/455 |
| 5,658,784 A | * | 8/1997 | Eckner et al. ............. 435/325 |
| 5,739,011 A | * | 4/1998 | Anderson et al. ......... 435/69.6 |

FOREIGN PATENT DOCUMENTS

| | | | |
|---|---|---|---|
| EP | 0960939 A2 | * | 1/1999 |
| JP | 11318478 | * | 11/1999 |
| WO | WO 96 35774 A | | 11/1996 |

OTHER PUBLICATIONS

Kelman et al. Gene 166:177–178, 1995.*
Mullins JJ et al. Hypertension 22:630–633, 1993.*
Cameron ER. Molecular Biotechnology 7:253–265, 1997.*
Hammer RE et al. Cell 63:1099–1112. 1990.*
Seidel GE. J. Anim. Sci. 71(Suppl. 3):26–33, 1993.*
Kiefer H et al. Biochemistry 35: 16077–16084, 1996.*
Kuusinen A et al. Eur. J. Biochem. 233: 720–726, 1995.*
LaVallie et al. Current Opinion in Biotechnology 6:501–506, 1995.*
Cao et al. The Journal of Biological Chemistry 271:29461–29467, 1996.*
Roth, M.B. et al.: "A Conserved Family of Nuclear Phosphoproteins Localized to Sites of Polymerase II Transcription" The Journal Of Cell Biology, vol. 115, No. 3, Nov. 1991, pp. 587–596.
Sim, B. Kim Lee, et al.: "A Recombinant Human Angiostatin Protein Inhibits Experimental Primary and Metastatic Cancer" Cancer Research, vol. 57, Apr. 1, 1997, pp. 1329–1334.
Chalfie, M. et al.: "Green Fluorescent Protein as a Marker for Gene Expression" Science, vol. 263, Feb. 11, 1994, pp. 802–805.
Folkman, J.: "What Is the Evidence That Tumors Are Angiogenesis Dependent?" Journal Of The National Cancer Institute, vol. 82, No. 1, Jan. 3, 1990, pp. 4–6.
Kain, S.R. et al.: "Green Fluorescent Protein as a Reporter of Gene Expression and Protein Localization" Biotechniques, vol. 19, No. 4, 1995, pp. 650–655.
Drickamer, K. et al.: "Biology of Animal Lectins" Annu. Rev. Cell Biol., vol. 9, 1993, pp. 237–264.
Sulkowski, E.: "Purification of proteins by IMAC" Trends In Biotechnology, vol. 3, No. 1, Jan. 1985, pp. 1–7.
Lönnerdal, B. et al.: "Metal Chelate Affinity Chromatography of Proteins" Journal Of Applied Biochemistry, vol. 4, 1982, pp. 203–208.
Porath, Jerker et al.: "Metal chelate affinity chromatography, a new approach to protein fractionation" Nature, vol. 258, Dec. 18, 1975, pp. 598–599.
Wilson, I.A. et al.: "The Structure of an Antigenic Determinant in a Protein" Cell, vol. 37, Jul. 1984, pp. 767–778.
Vaughan, T.J. et al.: "Human Antibodies with Sub–nanomolar Affinities Isolated from a Large Non–immunized Phage Display Library" Nature Biotechnology, vol. 14, Mar. 1996, pp. 309–314.
Takemoto, Yoshihiro et al: "Expression plasmid vectors with convenient subcloning sites in lambda–gt11 that efficiently produce detectable tagged proteins." DNA and Cell Biology, vol. 16, No. 7, 1997, pp. 893–896.
Pathak, Rahul, et al: "A dual affinity tag on the 64–kDa Nlt1p subunit allows the rapid characterization of mutant yeast oligosaccharyl transferase complexes." Archives of Biochemistry and Biophysics, vol. 338, No. 1, 1997, pp. 1–6.
Strugnell, S.A., et al: "A modified pGEX vector with a C–terminal histidine tag: Recombinant double–tagged protein obtained in greater yield and purity." Analytical Biochemisty, vol. 254, No. 1, 1997, pp. 147–149.
Robeva, A. S. et al: "Double tagging recombinant $A_1$–and $A_{2A}$ adenosine receptors with hexahistidine and the FLAG epitope. Development of an efficient generic protein purification procedure." Biochemical Pharmacology, vol. 51, 1996, pp. 545–555.
Parola, Anthony L. et al: "Site–specific fluorescence labeling of the beta2 adrenergic receptor amino terminus." Analytical Biochemistry, vol. 254, No. 1, 1997, pp. 88–95.
Winkler, G. Sebastiaan et al: "Affinity purification of human DNA repair/transcription factor TFIIH using epitope–tagged xeroderma pigmentosum B protein." Journal of Biological Chemistry, vol. 273, No. 2, 1998, pp. 1092–1098.

* cited by examiner

*Primary Examiner*—Dave T. Nguyen
*Assistant Examiner*—Ram R. Shukla
(74) *Attorney, Agent, or Firm*—Townsend and Townsend and Crew LLP

(57) ABSTRACT

The present invention provides improved methods for detection of recombinant proteins. The fusion proteins of the invention comprise a capture tag sequence, a detection tag sequence, and polypeptide sequence of interest.

15 Claims, 6 Drawing Sheets c-terminus Double Tagged Angiostatin

Angiostatin HA-FLAG    4 alanine spacer        pMB 281

YPYDVPDYAAAAADYKDDDDK

Angiostatin FLAG-HA    4 alanine spacer        pMB 281.1

DYKDDDDKAAAAYPYDVPDYA

Angiostatin HA-FLAG    10 alanine spacer       pMB 282

YPYDVPDYAAAAAAAAAADYKDDDDK

Angiostatin FLAG-HA    10 alanine spacer       pMB 282.1

DYKDDDDKAAAAAAAAAAYPYDVPDYA

FIG. 1.

DUAL-TAGGED PROTEINS AND THEIR USES

This application claims the benefit of U.S. Provisional Application No. 60/079,125, filed Mar. 23, 1998, the disclosure of which is incorporated by reference.

FIELD OF THE INVENTION

The present invention relates to dual-tagged recombinant fusion proteins. The fusion proteins of the invention are conveniently isolated and quantified, particularly in tissues from genetically modified animals.

BACKGROUND OF THE INVENTION

Methods for isolating and/or detecting recombinant proteins of interest are useful in a number of applications. For instance, sensitive detection of transgene products in genetically engineered animals is important in determining the tissues in which transgene expression occurs. The proteins can be detected using a binding ligand (e.g., an antibody) that specifically recognizes the desired protein. In most cases, this procedure requires raising antibodies that are specifically immunoreactive with the desired protein. To avoid this requirement, various tags which can be fused to the protein of interest have been developed. For instance, the tags may include a unique epitope for which antibodies are readily available. Other methods include use of tags which incorporate metal-chelating amino acids.

Single epitope tags and other related tags do not necessarily provide sufficient sensitivity to allow detection of transgene products in tissues of animals, however. Thus, what is needed in the art are more sensitive methods of detecting recombinant proteins in vivo and in vitro that are fast, cheap, and easy to carry out. The present invention provides these and other advantages.

SUMMARY OF THE INVENTION

The present invention provides fusion proteins and nucleic acids encoding them. The fusion proteins of the invention comprise a polypeptide sequence of interest, a capture tag sequence, and a detection tag sequence. The capture tag sequence and the detection tag sequence are each heterologous to the polypeptide sequence of interest. In some embodiments, either the capture tag sequence or the detection tag sequencecan be an 30 epitope tag. An exemplary capture tag sequence is DYKDDDDK (SEQ ID NO:1). AN exemplary detection tag sequence is YPYDVPDYA (SEQ ID NO:2).

The two tags can be positioned in a number of ways with respect to each other and the polypeptide sequence of interest. For instance, the capture tag sequence and the detection tag sequence can be positioned at the C terminus of the polypeptide sequence of interest. In addition, the fusion proteins of the invention can comprise linkers between the various components. For instance, the capture tag sequence and the detection tag sequence can be linked to each other through an oligopeptide linker. The linker may consist of less than about 15 amino acid residues, usually between about 4 and about 10 amino acids. The linker may comprise alanine residues. In some embodiments, the capture tag sequence, the detection tag sequence, or a combination thereof, can be linked to the polypeptide of interest through an oligopeptide linker.

The particular protein detected in the invention is not critical. In some embodiments the polypeptide of interest can be angiostatin.

The fusion proteins of the invention can be detected in an animal that comprises a nucleic acid molecule encoding the fusion protein. Typically, the assays of the invention include capturing the fusion protein in a sample from the animal with a compound that specifically binds the capture tag sequence; and then detecting the fusion protein in the sample with a second compound that specifically binds the detection tag sequence. The step of capturing can be carried out by contacting the sample with an antibody that specifically binds the capture tag sequence. The step of detecting can be carried out by contacting the sample with an antibody that specifically binds the detection tag sequence. The sample may be a tissue sample, such as lung tissue. The animal can be a transgenic or genetically engineered mouse.

DEFINITIONS

As used herein a "capture tag sequence" is a sequence of amino acid residues which can be used to isolate or remove a fusion protein of the invention from a complex mixture. Typically, a capture tag will be a sequence of amino acids that specifically binds a ligand (e.g., an antibody) and thus allows the fusion protein to be isolated from the mixture. Examples of various capture tags are set forth in detail below.

As used herein a "detection tag sequence" is a sequence of amino acid residues which can be used to detect the presence of a fusion protein of the invention, once the protein is isolated using the capture tag sequence. Any of a number of means may be used to detect the detection tag. The detection tag sequence can be directly detected (e.g., by fluorescence) or indirectly detected using a detectable ligand that specifically binds the detection tag. Example of various detection tags are set forth in detail below.

A "fusion protein" of the invention is a polypeptide sequence containing two, different heterologous sequences (e.g., a capture tag sequence and a detection tag sequence). The various components may be linked through linker sequences.

A polynucleotide or polypeptide sequence is "heterologous to" a second polynucleotide or polypeptide sequence if it is entirely synthetic, originates from a foreign species, or, if from the same species, is modified from its original form.

The phrases "specifically binds" refers to a binding reaction between a capture or detection ligand and an amino acid sequence, which binding is determinative of the presence of the amino acid sequence in the presence of a heterogeneous population of proteins and other biologics. Thus, under designated conditions, the capture or detection ligand binds preferentially to the particular sequence and does not bind in a significant amount to other amino acid sequences present in the sample. This interaction may also be referred to as "specifically immunoreactive", when referring to reaction between an epitope and an antibody (e.g., in the case of epitope tags).

The phrases "nucleic acid" or "polynucleotide" refer to a single or double-stranded polymer of deoxyribonucleotide or ribonucleotide bases. It includes cDNA, self-replicating plasmids, infectious polymers of DNA or RNA and non-functional DNA or RNA.

Two nucleic acid sequences or polypeptides are said to be "identical" if the sequence of nucleotides or amino acid residues, respectively, in the two sequences is the same when aligned for maximum correspondence as described below.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. Stringent conditions for a standard Southern hybridization will include at least one wash (usually 2) in 0.2×SSC at a temperature of at least about 50° C., usually about 55° C., for 20 minutes, or equivalent conditions.

BRIEF DESCRIPTION OF THE DRAWINGS

FIG. 1 illustrates various embodiments of the C-terminus double tagged proteins (SEQ ID NO: 3–6) of the invention.

DETAILED DESCRIPTION

Figure 2:
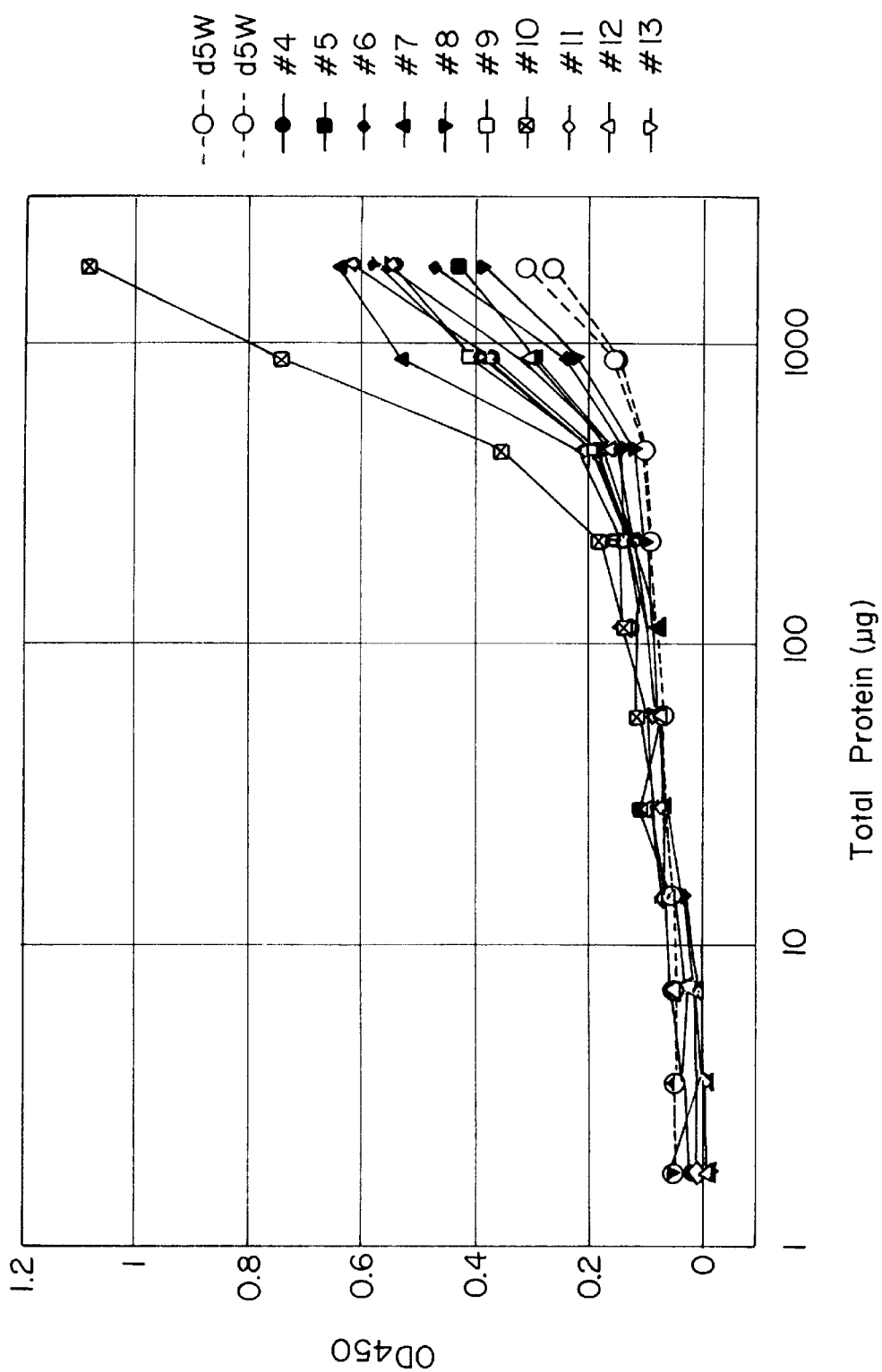
FIG. 2 shows the results from a FLAG-HA ELISA used to detect angiostatin-FLAG-HA protein in lung homogenates from mice. The OD values obtained for each lung sample are plotted as a function of total protein assayed.

The present invention is directed to compositions and methods for use in isolating and/or detecting recombinantly produced, dual-tagged fusion proteins in a variety of contexts. The proteins of the invention are particularly useful for sensitive detection of proteins in samples (e.g., tissue samples) from genetically engineered animals.

The capture and detection tags can be positioned in a number of ways with respect to the polypeptide sequence of interest. For instance, each tag can be placed at either the N- or C-terminus of the polypeptide sequence. In these embodiments, the tags can be positioned at the same or different ends of the polypeptide of interest. Alternatively, either or both tags can be positioned within the polypeptide sequence of interest. For instance, DNA encoding either or both tags, along with appropriate splicing sequences, may be placed within an intron included in the DNA sequence encoding the polypeptide of interest (see, e.g., U.S. Pat. No. 5,652,128). This creates a new construct including a new exon which encodes the tag sequence.

In some embodiments, the two tags are placed at the C-terminus of the polypeptide sequence with a spacer or linker sequence between them. The linker sequence can be any length sufficient to allow binding ligands specific for each tag to bind the target. The linker is usually less than about 30 amino acid residues in length, but can be less than about 20, or more usually less than about 15, even more commonly, 10 or less, such as 9, 8, 7, 6, 5 or 4 residues in length. The amino acids residues used in the linkers are not critical to the invention, but are typically chosen not to be cross-reactive with the capture or detection sequences and to have relatively small side chains. Suitable residues include, for instance, alanine, glycine, valine, leucine, isoleucine, and the like.

In addition, in some embodiments, a linker sequence can be included between the polypeptide of interest and the tags. In these embodiments, the spacer is designed to ensure that either or both tags are exposed, if the C- or N-terminus is buried in the folded protein. The linker sequence in these embodiments can be the same as that used between the tags.

Capture Tag Sequence

As noted above, the capture tag sequence in the fusion proteins of the invention is any sequence of amino acids that can be used to isolate the protein from a complex mixture. The particular capture tag used is not critical to the invention. Typically, the capture tag is chosen such that it can be used to concentrate the fusion protein before detection.

The capture tags of the invention are usually a sequence specifically bound by capture ligand that allows the fusion protein to be isolated from a complex mixture. In some embodiments the capture tag is an epitope tag and an antibody specifically immunoreactive with the epitope tag is used to isolate the protein. A number of epitope tags are known in the art, examples include, myc (Roth et al, *J. Cell Biol.* 115:587–596 (1991), HA, derived from the influenza hemagglutinin protein (Wilson, et al., *Cell,* 37:767 (1984), FLAG (International Biotechnologies Inc. (IBI), Kodak, New Haven, Conn., see, U.S. Pat. Nos. 4,793,004 and 4,851,341), IRS (RYIRS (SEQ ID NO: 7) or IRS antibodies available from BABCO), His (4, 5, or 6 histidine residues (SEQ ID NO: 8–10); or RGSHHHH (SEQ ID NO:11), antibodies available from Quiagen or BABCO) AU1 (DTYRYI (SEQ ID NO: 12), antibodies available from BABCO), AU5 (TDFLYK (SEQ ID NO: 13), antibodies available from BABCO), glu-glu (a 9 amino acid epitope from polyoma virus medium T antigen, EEEEYMPME (SEQ ID NO: 14), antibodies available from BABCO), KT3 (an 11 amino acid epitope from the SV40 large T antigen, KPPTPPPEPET (SEQ ID NO: 15), antibodies available from BABCO), T7 (an 11 amino acid leader peptide from T7 major capsid protein, antibodies available from Novagen), S-TAG (Novagen), HSV (an 11 amino acid peptide from herpes simplex virus glycoprotein D, antibodies available from Novagen), VSV-G (an 11 amino acid epitope from the carboxy terminus of vesicular stomatitis virus glycoprotein, YTDIEMNRLGK (SEQ ID NO: 16), antibodies available from Boerhringer Mannheim), Anti-Xpress (8 amino acid epitope, DLYDDDK (SEQ ID NO:17), antibodies available from Invitrogen), and V5, (14 amino acid epitope from paramyxovirus, GKPIPNPLLGLDST (SEQ ID NO: 18), antibodies available from Invitrogen).

In most instances, the antibody used to capture the fusion protein is readily available. The antibody may be a whole antibody or an antibody fragment. It may be polyclonal or monoclonal, and it may be produced by challenging an organism (e.g. mouse, rat, rabbit, etc.) with the desired epitope tag sequence. If necessary, one of skill can make the appropriate antibody using well known techniques (see, e.g. *Methods in Cell Biology Volume* 37: *Antibodies in Cell Biology,* Asai. ed. Academic Press, Inc. New York (1993); and *Basic and Clinical Immunology* 7th Edition, Stites & Terr, eds. (1991)). Alternatively, the antibody may be produced de novo using recombinant DNA methodology. The antibody can also be selected from a phage display library screened against the protein (see, e.g. Vaughan et al. (1996) *Nature Biotechnology,* 14: 309–314 and references therein).

In other embodiments, leucine zipper motifs can be incorporated into the proteins. These embodiments are based on the strong interactions of peptide segments of certain protein pairs which are able to bind DNA and thus are capable of modulating transcription. Examples of pairs of leucine zipper containing proteins include the fos gene product and the junt gene product. Examples of particular sequences for this purpose include amino acid positions 285 to 324 of the c-Jun protein and positions 162 to 201 of the v-Fos protein (see, e.g., U.S. Pat. No. 5,643,731). In these embodiments, one of the sequences is incorporated into the fusion protein of the invention and the other is used as a capture ligand attached to a solid surface.

A capture tag of the invention may also include metal-chelating amino acids (see, e.g., Porath, et al., *Nature* 258:598–599 (1975) Lonnerdal and Keen, *J. Appl. Biochem.* 4:203–208 (1982), Sulkowski, *Trends in Biotechnology* 3:1–7 (1985) and U.S. Pat. No. 5,047,513). As used herein, a metal-chelating amino acid is one which is capable of participating in metal binding, i.e., an amino acid that is capable of forming a chelate or complex with a metal ion. Such amino acids include: glycine, tyrosine, cysteine, histidine, arginine, lysine, asparagine and methionine. Usually, histidine is used. Typically, from two to about ten metal-chelating amino acids are incorporated into the fusion protein. More preferably, about six metal-chelating amino acids are incorporated into the protein.

Generally, metal chelate separation methods take advantage of the reversible interaction between metal ions (such as, for example, $Cu^{2+}$, $Zn^{2+}$, $Ni^{2+}$, etc.) and electron donor groups situated on the surface of proteins, especially the imidazole side-chain of histidine. By immobilizing metal ions on a solid support or matrix through the use of a chelating ligand (i.e., by forming a chelate resin), a protein having an accessible electron donor group can be separated from protons lacking such groups. The protein binds to the immobilized metal ions when the pH is such that the electron donor group is at least partially unprotonized. The bound protein can subsequently be eluted using a number of different techniques such as, for example, by competitive elution, by lowering the pH or, by using strong chelating agents.

Metal ions suitable for use in accordance with the present purification method include, but are not limited to, the first-row transition metals. The first-row transition metals include, for example, $Cu^{2+}$, $Zn^{2+}$, $Ni^{2+}$, $Co^{2+}$ and $Fe^{3+}$. In a presently preferred embodiment, $Ni^{2+}$, $Cu^{2+}$ and $Zn^{2+}$ are the metal ions used. It has been found that these metals readily form a complex or chelate with metal-chelating amino acids and thus, they can be used to separate those proteins having a metal-chelating amino acid(s) from those which do not.

Other means of specifically binding the expressed fusion proteins can be used as well. For instance, specific lectin domains can be incorporated into the capture tag sequence. Cognate carbohydrates can then be used to capture the fusion proteins (see, e.g., Drickamer et al., Biology of animal lectins, *Annu Rev Cell Biol* 9:237–64 (1993).

The capture tag sequences of the invention are used to isolate the fusion proteins according to well known techniques, depending upon the particular capture tag used. Typically, a binding ligand (e.g., antibody, leucine zipper sequence, metal, and the like) is covalently bound to a solid surface and the sample comprising the fusion protein is contacted with the solid surface. Many methods for immobilizing biomolecules to a variety of solid surfaces are known in the art. For instance, the solid surface may be a membrane (e.g., nitrocellulose), a microtiter dish (e.g., PVC or polystyrene) or a magnetic bead. The desired component may be covalently bound or non-covalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. Also included are substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See for example Immobilized Enzymes, Ichiro Chibata, Halsted Press, New York, 1978, and Cuatrecasas, *J. Biol. Chem.* 245 3059 (1970).

In addition to covalent bonding, various methods for noncovalently binding a ligand can be used. Non-covalent binding is typically nonspecific absorption of a compound to the surface. Typically, the surface is blocked with a second compound to prevent nonspecific binding of various components in the sample. Various solid surfaces for use in noncovalent attachment of components are reviewed in U.S. Pat. Nos. 4,447,576 and 4,254,082.

In preferred embodiments, materials commonly used in affinity and gel chromatography are conveniently used. Examples of such materials include, for instance, dextran, agarose, cellulose, polystyrene, polyacrylamide, and their derivatives. Alternatively, the binding ligand can be bound to paramagnetic beads, which can then be used to separate the fusion protein according to known techniques. Such beads are available, for instance, from Dynal, Inc. Lake Success, N.Y. Brun et al. Blood 1990;76(11):2397–2403. For instance, in some embodiments, biotin-strepavidin binding is used to attach capture antibodies to the beads. Methods for use of paramagnetic beads are described, for instance, in U.S. Pat. No. 4,910,148, Metzger et al. *Ann. N.Y. Acad. Sci* 651:75–77 (1992), Rasmussen et al. *Journal of Immunological Methods* 146:195–202 (1992), and Funderud et al. *European Journal of Immunology* 20:201–206 (1990).

Detection Tag Sequence

After the fusion protein is concentrated using the capture tag, it is detected using the detection tag. Any number of means of detecting the desired protein molecule can be used for this purpose. The detection tag can be directly or indirectly detected. Examples of directly detectable detection tags include fluorescent and chemiluminescent polypeptide sequences (e.g., green fluorescent protein, see, e.g., Kain et al. *BioTechniques* 19:650–655 (1995), Chalfie et al., Science 263:802–805 (1994), and luciferase, see, e.g., U.S. Pat. No. 5,283,179). If indirectly detected, the detection tag sequence is bound by a ligand (e.g., leucine zipper pair sequences, epitope tags/antibodies or metal binding domains as described above) which incorporates a detectable moiety.

The detectable ligand may be labeled by any one of several methods. Examples of labels include, but are not limited to, the following: radioisotopes (e.g., $^3H$, $^{14}C$, $^{35}S$ $^{125}I$, $^{131}I$), fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, polypeptide sequences recognized by a secondary antibody and the like. In some embodiments, labels are attached by spacer arms of various lengths, e.g., to reduce potential steric hindrance.

A preferred method of detecting the ligand is through electrochemiluminescence (IGEN International, Inc., Gaithersburg, Md. 20877). Electrochemiluminescence is the process by which light generation occurs when a low voltage is applied to an electrode, triggering a cyclical oxidation and reduction reaction of a ruthenium metal ion bound to the compound to be detected. The ruthenium ion is bound in a chelate of tris-(bipyridine). A second reaction component, tripropylamine (TPA), present in the assay buffer in vast molar excess, is consumed in the oxidation process and the ruthenium chelate is recycled. In the assays, the labeled component is captured on a solid surface, the second oxidation reaction component, TPA, is introduced into the flow cell and a voltage is applied. The TPA reduces the ruthenium, which receives the electron in an excited state and then decays to the ground state releasing a photon in the process.

Some assay formats do not require the use of labeled components. For instance, agglutination assays can be used to detect the presence of the fusion proteins. In this case, ligand-coated particles are agglutinated by samples comprising the target fusion proteins. In this format, none of the components need be labelled and the presence of the fusion protein is detected by simple visual inspection.

In the case of epitope tags, the presence of particular detection tag sequences can be detected using several well recognized immunoassay protocols. For a review of the general procedures useful in immunoassays, see, *Basic anid Clinical Immunology* 7th Edition (D. Stites and A. Terr ed.) 1991. For example, in a typical ELISA-based detection assay, the fusion protein is bound to a solid surface using the capture tag and a labeled antibody that specifically immnunoreacts with the detection tag is used to detect and quantify the fusion protein. Other formats could also be used such as Western blots, or liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:3441(1986).

Polypeptide Sequence of Interest

The particular polypeptide sequence to be detected is not critical to the invention. The polypeptides will typically be those of interest as therapeutic polypeptides used in gene therapy. The polypeptides may be those used to treat a variety of diseases such as congenital genetic diseases, acquired genetic diseases (e.g., cancer), viral diseases (e.g., AIDS, mononucleosis, herpes virus infection, cytomegalovirus infection, papillomovirus infection) or to modify the genome of selected types of cells of a patient for any therapeutic benefit. In the example below, the methods of the invention are used to detect the presence of recombinant angiostatin in mouse tissues.

Expression of Fusion Proteins

The fusion proteins of the invention can be expressed in a number of systems including genetically engineered animals or plants, or in cells such as bacteria, yeast, insect, plant and mammalian cell cultures. It is expected that those of skill in the art are knowledgeable in the numerous expression systems available for expression of the DNA encoding recombinant polypeptides. No attempt to describe in detail the various methods known for the expression of proteins in prokaryotes or eukaryotes will be made. Much of the nomenclature and general laboratory procedures required for these procedures can be found in Sambrook, et al., *Molecular Cloning: A Laboratory Manual* (2nd Ed.), Vol. 1–3, Cold Spring Harbor Laboratory, Cold Spring Harbor, N.Y., 1989.

In brief summary, the expression of natural or synthetic nucleic acids encoding the polypeptides for detection will typically be achieved by operably linking nucleic acids encoding the fusion protein to a promoter (which is either constitutive or inducible), followed by incorporation into an expression vector. The vectors can be suitable for replication and integration in either prokaryotes or eukaryotes or both. Typical expression vectors contain transcription and translation terminators, poly A addition sites, introns with splice sites, initiation sequences, and promoters useful for regulation of the expression of the DNA encoding the fusion proteins. To obtain high level expression of a cloned gene, it is desirable to construct expression plasmids which contain, at the minimum, a promoter to direct transcription, a poly A sequence, and a binding site for translational initiation.

Expression systems for expressing the fusion proteins are available using *E. coli*, Bacillus sp. (Palva, I. et al., 1983, *Gene* 22:229–235; Mosbach, K. et al., *Nature*, 302:543–545 and Salmonella. Synthesis of heterologous proteins in yeast is also well known and described. *Methods in Yeast Genetics*, Sherman, F., et al., Cold Spring Harbor Laboratory, (1982) is a well recognized work describing the various methods available to produce heterologous polypeptides in yeast. The polynucleotides encoding the fusion proteins can also be ligated to various expression vectors for use in transforming mammalian or insect cell cultures. Illustrative examples of mammalian cell lines include VERO, COS, and HeLa cells, Chinese hamster ovary (CHO) cell lines, and various cell lines as described in the American Type Culture Collection Catalogue of Cell Lines and Hybridomas (7th edition, 1992). Suitable insect cell lines include mosquito larvae, silkworm, armyworm, moth and Drosophila cell lines.

In most preferred embodiments, the constructs encoding the fusion protein of the invention are used to produce a genetically engineered animal or plant. For production of genetically engineered animals (e.g., mice, rats, guinea pigs, rabbits, and the like) the construct can be introduced into cells in vitro or iii vivo. These nucleic acids can be inserted into any of a number of well known vectors for the transfection of target cells and organisms.

A number of methods suitable for delivery of desired nucleic acids to animal cells are known. Such methods include, for example liposome-based gene delivery (Debs and Zhu (1993) WO 93/24640; Mannino and Gould-Fogerite (1988) *Bio Techniques* 6(7): 682–691; Rose U.S. Pat No. 5,279,833, Brigham (1991) WO 91/06309; and Felgner et al. (1987) *Proc. Natl Acad. Sci. USA* 84: 7413–7414). Cationic lipids useful in these methods include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used include DOTIM (also called BODAI) (Solodin et al., (1995) *Biochem.* 34: 13537–13544), DDAB (Rose et al., (1991) *BioTechniques* 10(4):520–525), DOTMA (U.S. Pat. No. 5,550,289), DOTAP (Eibl and Wooley (1979) *Biophys. Chem.* 10:261–271), DMRIE (Felgner et al. (1994) *J. Biol. Chem.* 269(4): 2550–2561), EDMPC (commercially available from Avanti Polar Lipids, Alabaster, Al.), DC-Chol (Gau and Huang (1991) *Biochem. Biophys. Res. Comm.* 179:280–285), DOGS (Behr et al. (1989) *Proc. Nat'l. Acad Sci. USA*, 86:6982–6986), MBOP (also called MeBOP) (WO 95/14651), and those described in WO 97/00241.

Neutral lipids include, for example, dioleoyl phosphatidylethanolamine (DOPE), Hui et al. (1996) *Biophys. J.* (71): 590–599 and cholesterol, Liu et al. (1997) *Nat. Biotech.* (15): 167–173. The specific cationic and neutral lipids used will depend on the target cell type and mode of administration. For example, for intravenous delivery to lung vascular endothelial cells. the transfection complex is prepared from liposomes having a 1:1 molar ratio of DOTIM and cholesterol, complexed with plasmid DNA in a 1:6 ratio (µg DNA:nmole cationic lipid). See WO 96/40962.

The lipid mixtures typically are prepared in chloroform, dried, and rehydrated in, e.g., 5% dextrose in water or a physiologic buffer to form liposomes. Low ionic strength solutions are preferred. Liposomes may be LUVs, MLVs, or SUs. Usually, the liposomes formed upon rehydration are predominantly MLVs, and SUVs are formed from them by sonication or by extrusion through membranes with pore sizes ranging from 50 to 600 nm to reduce their size. Most preferably, the liposomes are extruded through a series of membranes with decreasing pore sizes, e.g., 400 nm, 200 nm and 50 nm. The resulting liposomes are mixed with plasmid DNA to form complexes able to transfect target cells of interest.

Replication-defective retroviral vectors harboring a desired polynucleotide sequence as part of the retroviral genome can also be used to deliver the nucleic acids encoding the fusion proteins of the invention (see, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)). Widely used retroviral vectors include those based upon Moloney murine leukemia virus (MMuLV), gibbon ape leukemia virus (GaLV), simian immunodeficiency virus (SIV), human immunodeficiency virus (HIV), and combinations thereof See, e.g., Buchscher et al. (1992) *J. Virol.* 66(5) 2731–2739; Johann et al. (1992) *J. Virol* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al., *Gene Therapy* (1994) supra).

Adenoviral vectors are also commonly used for introduction of nucleic acids into mammals. See, e.g., Berns et al.

(1995) *Ann. NY Acad. Sci.* 772: 95–104; Ali et al. (1994) *Gene Ther.* 1: 367–384; and Haddada et al. (1995) *Curr. Top. Microbiol Immunol.* 199 (Pt 3): 297–306 for review. Adeno-associated virus (AAV)-based vectors are also used to transduce cells with target nucleic acids, See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.*, 4:2072–2081; Hermonat and Muzyczka (1984) *Proc. NatL Acad Sci. USA,* 81:6466–6470; McLaughlin et al. (1988) and Samulski et al. (1989) *J. Virol.,* 63:03822–3828. Cell lines that can be transformed by rAAV include those described in Lebkowski et al. (1988) *Mol. Cell. Biol.,* 8:3988–3996.

The nucleic acids, alone or in combination with other suitable components, can be made into aerosol formulations (i.e., they can be "nebulized") to be administered via inhalation (see, U.S. Pat. No. 5,641,662). Aerosol formulations can be placed into pressurized acceptable propellants, such as dichlorodifluoromethane, propane, nitrogen, and the like.

After expression in the genetically engineered animal, the fusion protein is detected in a sample from the animal. The sample can be a biological fluid such as whole blood, plasma, serum, nasal secretions, sputum, salvia, urine, sweat, transdermal exudates, cerebrospinal fluid, or the like. Alternatively, the sample may be whole organs, tissue or cells from the animal. Examples of sources of such samples include muscle, eye, skin, gonads, lymph nodes, heart, brain, lung, liver, kidney, spleen, solid tumors, macrophages, mesothelium, and the like.

EXAMPLES

The following examples are offered to illustrate, but not to limit the present invention.

Example 1

FLAG-HA ELISA

This example describes unro teins of the invention which include the octapeptide, FLAG(DYKDDDDK (SEQ ID NO:1)) as the capture tag sequence and the nonapeptide HA (YPYDVPDYA (SEQ ID NO:2)) as the tag sequence. The polypeptide of interest used in these experiments was angiostatin. Angiostatin is a naturally-occurring cleavage product of plasminogen, which is known to have anti-angiogenic activity (see, Folkman (1990) *J. Nat'l. Cancer Inst.* 82: 4–6 and Sim et al. (1997) *Cancer Res.* 57: 1329–1334).

The FLAG and HA sequences were fused to the carboxy terminus of angiostatin in several variations. Two constructs utilize a 4 amino acid spacer (AAAA (SEQ ID NO:19)) in two orientations: HA-spacer-FLAG (pMB281) and FLAG-spacer-HA (pMB281.1). The second two constructs utilized a longer spacer (10 alanines (SEQ ID NO:20)) in both orientations (see, FIG. 1).

A sandwich ELISA was used to detect the proteins. In brief, this sandwich ELISA uses the anti-FLAG M2 monoclonal antibody (IBI/Kodak) as a capture reagent and detection is achieved with a rabbit anti-HA peptide polyclonal (Santa Cruz Biotech.) and a goat anti-rabbit-HRP (Accurate). This assay has been shown to be specific for FLAG-HA tagged angiostatin expressed by transiently transfected 293 cells.

In vivo transfection experiment We wished to determine if the FLAG-HA ELISA in its current form was capable of detecting angiostatin-FLAG-HA protein present in lung homogenates prepared from C57/816 mice transfected IV with the lipid formulation MB112 (DOTIM:Cholesterol 1:1 molar ratio, 1:6, μgDNA:nrnole cationic lipid). In FIG. 2, the OD values obtained for each lung sample was plotted as a function of total protein assayed. As shown there, 10 out of 10 lung samples returned higher OD values than the D5W (5% dextrose in water (w/v)) control lung samples. This result demonstrated that the FLAG-HA ELISA was capable of detecting FLAG-HA tagged angiostatin present in these in vivo transfected lung homogenates.

Example 2

FLAG-HA ECL Assay (ORIGEN®)

Figure 3:
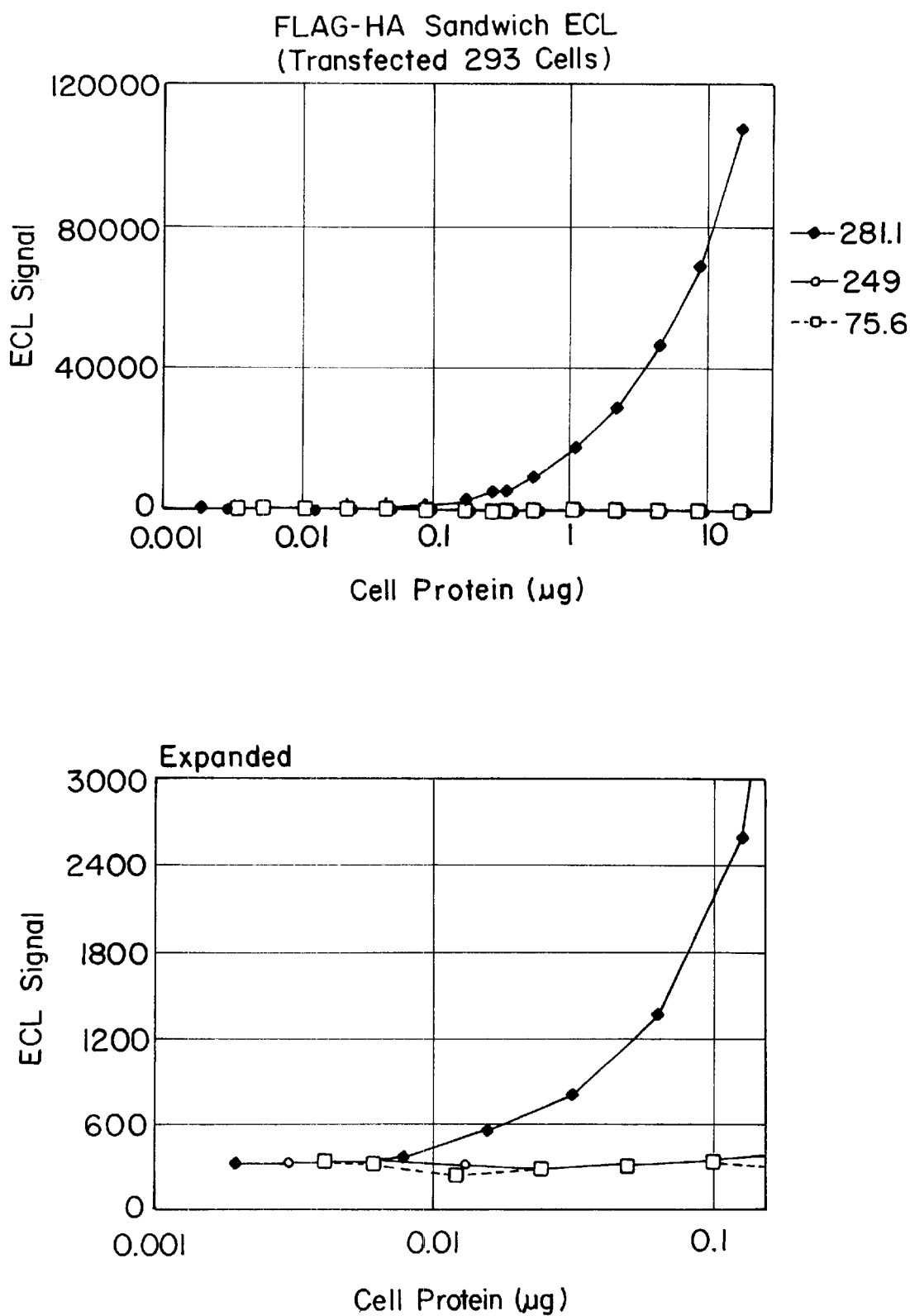
FIG. 3 shows a representative dilution curve for the FLAG-HA ECL assay, plotted as ECL signal versus amount of total protein assayed.
Figure 4:
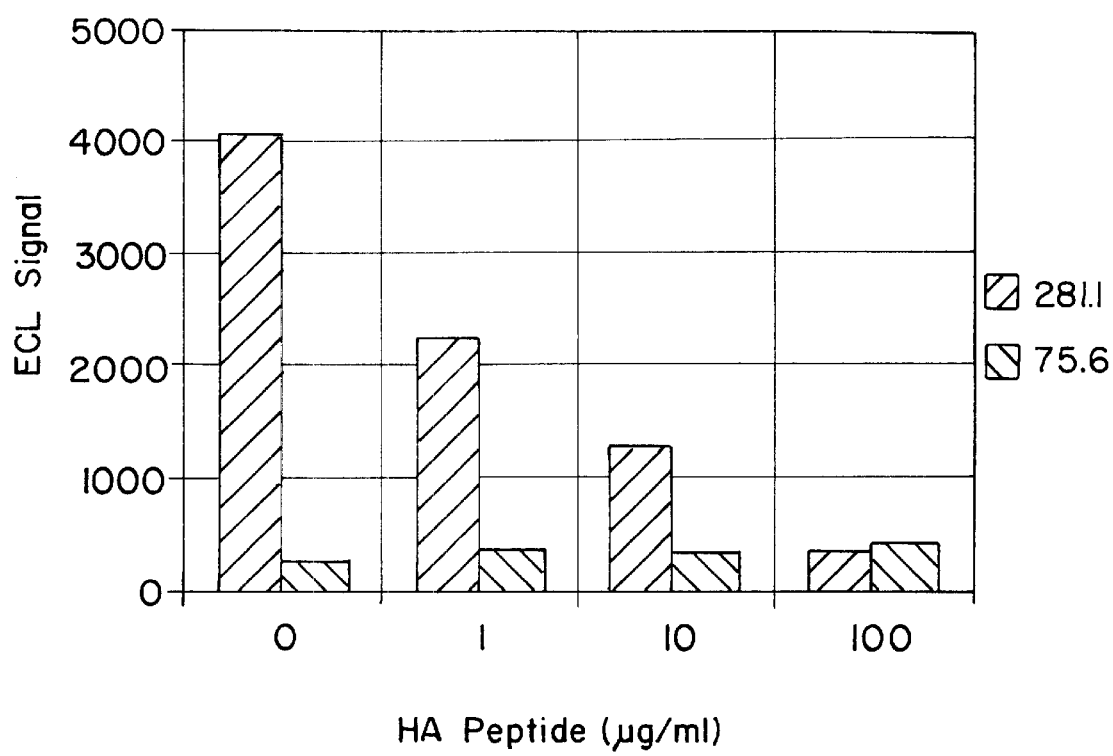
FIG. 4 shows that the ECL signal obtained with the angiostatin-FLAG-HA transfected lysate was inhibited by increasing concentrations of HA peptide.

This example describes an electrochemiluminescent (ECL)-based assay which mimics the FLAG-HA ELISA described in Example 1. This assay used biotinylated anti-FLAG M2 monoclonal antibody (IBI/Kodak) as a capture reagent while detection was achieved with a ruthenium labeled rabbit anti-HA peptide polyclonal antibody (Santa Cruz Biotech). Serial dilution experiments were performed to optimize the relative concentrations of capture and detection reagents. Lysates from 293 cells transiently transfected with pMB281.1 (angiostatin-FLAG-HA) were used as a source of double tagged protein for assay optimization. A representative dilution curve, plotted as ECL signal versus amount of total protein assayed is illustrated in FIG. 3. As shown, a positive signal (>2-fold above background) was obtained when less than 0.45 ug of total protein prepared from pMB28 1.1 transfected cells was assayed. However, lysates prepared from cells transfected with pMB249 (angiostatin-HA single tag) or pMB75.6 (vector backbone control) were not recognized. This result suggested that the assay was specific for the double tagged form of angiostatin. To further demonstrate specificity of the assay the analysis was repeated in the presence of increasing concentrations of HA peptide. FIG. 4 demonstrates that the ECL signal obtained with the angiostatin-FLAG-HA transfected lysate was inhibited by increasing concentrations of HA peptide. This finding supports the conclusion that the assay is specific for the epitope tagged angiostatin.

A standard curve can be generated using crude transfected 293 cell lysates as a source of double tagged angiostatin. In order to establish a quantitation standard for the FLAG-HA ECL assy, the concentration of tagged angiostatin in 293 transfected cell lysates was quantitated. This was accomplished using an immuno-based competition assay measuring the molar concentration of HA epitopes in the sample. An example of this analysis is shown in Table 1. Based on the HA peptide standard inhibition curve used for the ECL competition assay, the pMB28 1.1 transfected 293 cell lysate was calculated to contain 11.18 ug/ml angiostatin-FLAG-HA. Using this estimate of specific protein concentration, this lysate may be used as a relative quantitation standard for the FLAG-HA ECL assay.

TABLE 1

ECL Competition Assay
Quantitation of FLAG-HA Tagged Angiostatin in Transfected 293 Cells

| Plasmid ID | Equivalent HA peptide (pg/ml) | Equivalent Molar Conc. (pM) | Calculated Target Protein (ug/ml) | Total Protein (mg/ml)* | Target Protein Concentration (ug/mg total protein) |
|---|---|---|---|---|---|
| pMB75.6 | <90 | 0 | 0 | 1.533 | 0 |
| pMB249 | 65086 | 71594 | 3.08 | 1.618 | 1.9 |
| pMB281.1 | 236271 | 259899 | 11.18 | 1.466 | 7.7 |

In vivo Transfection Experiment

Figure 5:
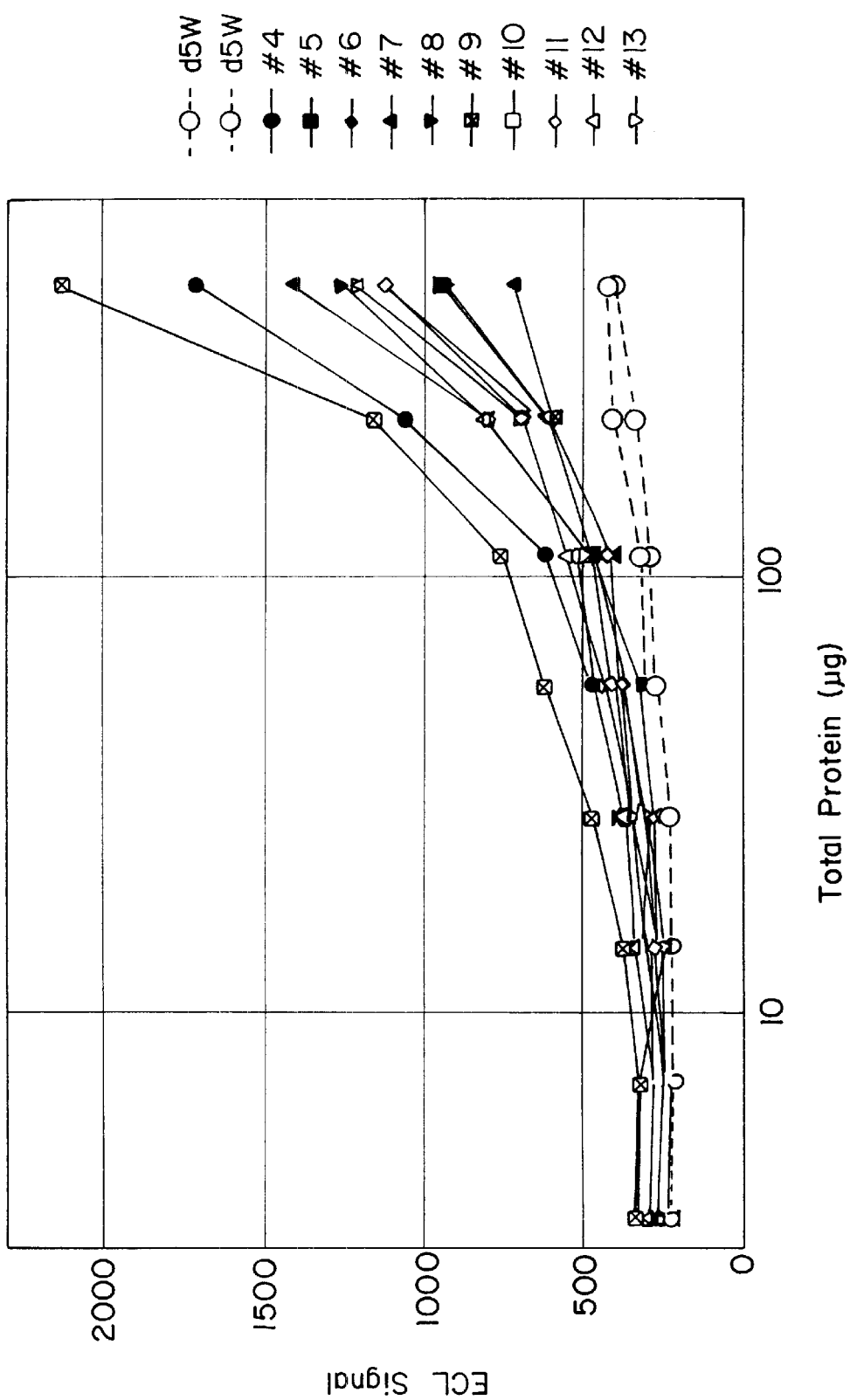
FIG. 5 shows the result of a FLAG-HA ECL assay used to measure angiostatin-FLAG-HA protein in lung homogenates from mice.

The FLAG-HA ECL assay was used to measure angiostatin-FLAG-HA protein in lung homogenates prepared from C57/B16 mice transfected IV with the lipid formulation MB112. All of the lung samples returned higher ECL values than the D5W control lung samples (FIG. 5). Therefore the FLAG-HA ECL assay is capable of detecting FLAG-HA tagged angiostatin present in transfected lung homogenates.

Figure 6:
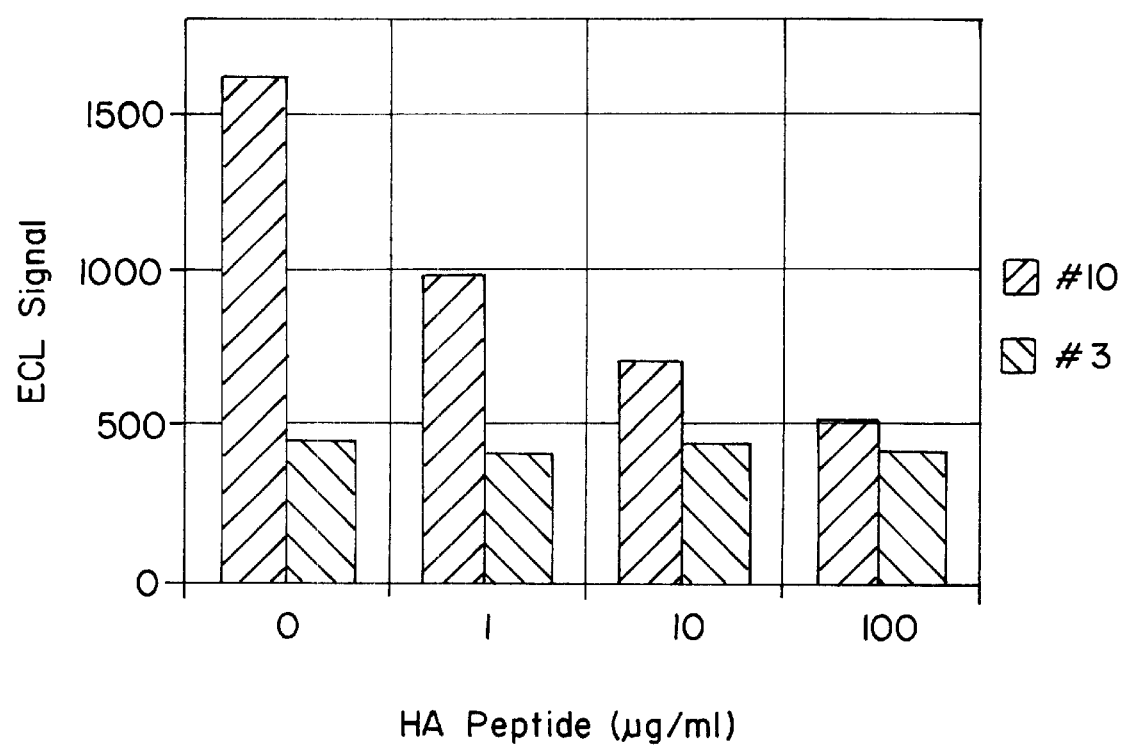
FIG. 6 shows that the ECL signal obtained with the positive lung homogenates was inhibited by increasing concentrations of HA peptide.

To demonstrate that the signal obtained with these lung homogenates is specific for the tagged angiostatin molecule, sample #10 which gave the highest ECL signal was re-tested in the presence of increasing concentrations of HA peptide. The results of this experiment are provided in FIG. 6. The ECL signal obtained with the positive lung homogenate (sample #10) decreases as the concentration of HA peptide increases. The signal obtained with a control lung homogenate (sample #3) is below background. These results support the conclusion that the assay specifically recognizes FLAG-HA tagged angiostatin in transfected mouse lung homogenates.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of detecting the expression of a fusion protein in a mammal, the method comprising:
   (a) introducing into the mammal a construct comprising a nucleic acid encoding the fusion protein, wherein the fusion protein encoded by the construct is expressed, said fusion protein comprising a polypeptide sequence of interest, a capture tag sequence, and a detection tag sequence, wherein the capture tag sequence and the detection tag sequence are each heterologous to the polypeptide sequence of interest;
   (b) capturing the fusion protein from a sample from the mammal with a compound that specifically binds the capture tag sequence; thereby prosuing a captured sample, and
   (c) detecting the fusion protein from in the captured sample of step b with a second compound that specifically binds the detection tag sequence,
   wherein detection of the fusion protein in the sample indicates the presence of the fusion protein in the mammal.

2. The method of claim 1, wherein the step of capturing is carried out by contacting the sample with an antibody that specifically binds the capture tag sequence.

3. The method of claim 2, wherein the capture tag sequence is DYKDDDDK (SEQ ID NO:1) DYKDDDDK.

4. The method of claim 1, wherein the step of detecting is carried out by contacting the sample with an antibody that specifically binds the detection tag sequence.

5. The method of claim 4 wherein the detection tag sequence is YPYDVPDYA (SEQ ID NO:2).

6. The method of claim 1, wherein the capture tag sequence and the detection tag sequence are positioned at the C terminus of the polypeptide sequence of interest.

7. The method of claim 1, wherein the capture tag sequence and the detection tag sequence are linked to each other through a oligopeptide linker.

8. The method of claim 7, wherein the linker consists of alanine residues.

9. The method of claim 7, wherein the linker consists of less than 16 amino acids.

10. The method of claim 9, wherein the linker consists of between 3 amino acids and 11 amino acids.

11. The method of claim 1, wherein the capture tag sequence, the detection tag sequence, or the combination thereof, is linked to the polypeptide sequence of interest through a oligopeptide linker.

12. The method of claim 1, wherein the polypeptide sequence of interest is angiostatin.

13. The method of claim 1, wherein the sample is a tissue sample.

14. The method of claim 13, wherein the tissue sample is lung tissue.

15. The method of claim of claim 1, wherein the mammal is a mouse.

* * * * *